(12) United States Patent
Ingber et al.

(10) Patent No.: US 10,731,123 B2
(45) Date of Patent: Aug. 4, 2020

(54) OPTICS CUP WITH CURVED BOTTOM

(71) Applicant: POCARED DIAGNOSTICS LTD., Rehovot (IL)

(72) Inventors: Gal Ingber, Oranit (IL); Martha J. Rogers, Bellville, OH (US)

(73) Assignee: POCARED Diagnostics LTD., Rehovot (IL)

( * ) Notice: Subject to any disclaimer, the term of this patent is extended or adjusted under 35 U.S.C. 154(b) by 72 days.

(21) Appl. No.: 15/824,538

(22) Filed: Nov. 28, 2017

(65) Prior Publication Data

US 2018/0080000 A1    Mar. 22, 2018

Related U.S. Application Data

(62) Division of application No. 14/102,742, filed on Dec. 11, 2013, now Pat. No. 9,862,920.

(60) Provisional application No. 61/735,737, filed on Dec. 11, 2012.

(51) Int. Cl.
| | |
|---|---|
| *B01L 3/00* | (2006.01) |
| *C12M 1/34* | (2006.01) |
| *G01N 21/03* | (2006.01) |
| *G01N 35/04* | (2006.01) |
| *G01N 21/64* | (2006.01) |

(52) U.S. Cl.
CPC ............. *C12M 41/36* (2013.01); *B01L 3/508* (2013.01); *G01N 21/0303* (2013.01); *B01L 2300/0809* (2013.01); *B01L 2300/0851* (2013.01); *G01N 2021/0382* (2013.01); *G01N 2021/6469* (2013.01); *G01N 2021/6482* (2013.01); *G01N 2035/0436* (2013.01); *G01N 2201/0655* (2013.01)

(58) Field of Classification Search
CPC .................. B01L 2300/0851; B01L 2300/168
See application file for complete search history.

(56) References Cited

U.S. PATENT DOCUMENTS

| | | | |
|---|---|---|---|
| 4,360,360 A | 11/1982 | Chiknas | |
| 4,406,547 A | 9/1983 | Aihara | |
| 4,449,821 A | 5/1984 | Lee | |
| (Continued) | | | |

FOREIGN PATENT DOCUMENTS

| | | |
|---|---|---|
| EP | 2618161 A1 | 7/2013 |
| GB | 2019563 A | 10/1979 |
| (Continued) | | |

OTHER PUBLICATIONS

Giana et al., "Rapid Identification of Bacterial Species by Flourescence Spectroscopy and Classification Through Principal Components Analysis" Journal of Flourescence, Nov. 2003, pp. 489-493, vol. 13, No. 6, Plenum Publishing Corporation.

*Primary Examiner* — Jonathan M Hurst
(74) *Attorney, Agent, or Firm* — The Webb Law Firm

(57) ABSTRACT

The present invention relates to a system for conducting the identification and quantification of micro-organisms, e.g., bacteria, in biological samples. More particularly, the invention relates to a system comprising a disposable cartridge and an optics cup or cuvette having a tapered surface; wherein the walls are angled to allow for better coating and better striations of the light. The system may utilize the disposable cartridge in the sample processor and the optics cup or cuvette in the optical analyzer, wherein the optics cup also has a floor in the shape of an inverted arch.

4 Claims, 11 Drawing Sheets

(56) References Cited

U.S. PATENT DOCUMENTS

| | | |
|---|---|---|
| 4,477,186 A | 10/1984 | Carlson |
| 4,509,856 A | 4/1985 | Lee |
| 4,556,636 A | 12/1985 | Belly et al. |
| 4,565,447 A | 1/1986 | Nelson |
| 4,634,576 A | 1/1987 | Galle et al. |
| 4,639,135 A * | 1/1987 | Borer .................... G01N 21/03 356/246 |
| 4,701,607 A | 10/1987 | El-Hanany et al. |
| 4,829,533 A | 5/1989 | Hallberg et al. |
| 4,849,177 A | 7/1989 | Jordan |
| 4,873,993 A | 10/1989 | Meserol et al. |
| 4,918,984 A | 4/1990 | Martinoli et al. |
| 5,029,245 A | 7/1991 | Keranen et al. |
| 5,314,825 A | 5/1994 | Weyrauch et al. |
| 5,424,036 A | 6/1995 | Ushikubo |
| 5,578,269 A | 11/1996 | Yaremko et al. |
| 5,605,665 A | 2/1997 | Clark et al. |
| 5,700,428 A | 12/1997 | Carlson |
| 5,797,147 A | 8/1998 | Young et al. |
| 6,027,695 A | 2/2000 | Oldenburg et al. |
| 6,515,745 B2 | 2/2003 | Vurens et al. |
| 6,559,941 B1 | 5/2003 | Hammer |
| 6,602,474 B1 | 8/2003 | Tajima |
| 6,767,511 B1 | 7/2004 | Rousseau |
| 6,773,922 B2 | 8/2004 | Jeng et al. |
| 6,824,741 B2 | 11/2004 | Sarstedt et al. |
| 6,831,740 B2 | 12/2004 | Herzinger et al. |
| 7,206,620 B2 | 4/2007 | Erickson et al. |
| 7,277,175 B2 | 10/2007 | Thompson et al. |
| 7,299,079 B2 | 11/2007 | Rebec et al. |
| 7,303,922 B2 | 12/2007 | Jeng et al. |
| 7,959,878 B2 | 6/2011 | Rousseau |
| 8,211,386 B2 | 7/2012 | Talmer et al. |
| 8,309,897 B2 | 11/2012 | Ingber |
| 8,519,358 B2 | 8/2013 | Ingber et al. |
| 2001/0040680 A1 | 11/2001 | Kubo et al. |
| 2003/0032173 A1 | 2/2003 | Farina et al. |
| 2005/0110980 A1 | 5/2005 | Maehara et al. |
| 2005/0110989 A1 | 5/2005 | Schermer et al. |
| 2005/0175502 A1 | 8/2005 | Rousseau et al. |
| 2005/0271550 A1 | 12/2005 | Talmer et al. |
| 2006/0013729 A1 | 1/2006 | Carey et al. |
| 2006/0120926 A1 | 6/2006 | Takada et al. |
| 2007/0037135 A1 | 2/2007 | Barnes et al. |
| 2007/0189925 A1 | 8/2007 | Blecka et al. |
| 2007/0224083 A1 | 9/2007 | Ouchi et al. |
| 2008/0003665 A1 | 1/2008 | Potyrailo et al. |
| 2008/0100837 A1 | 5/2008 | de Boer et al. |
| 2008/0151249 A1 | 6/2008 | Walker et al. |
| 2008/0297796 A1 | 12/2008 | Lukas et al. |
| 2008/0297798 A1 | 12/2008 | Wyssen |
| 2008/0318323 A1 | 12/2008 | Shintani et al. |
| 2009/0009757 A1 | 1/2009 | Mototsu et al. |
| 2009/0067280 A1 | 3/2009 | Ammann et al. |
| 2010/0200728 A1 | 8/2010 | Ingber |
| 2010/0208256 A1 | 8/2010 | Tang et al. |
| 2011/0008825 A1 | 1/2011 | Ingber et al. |
| 2011/0042582 A1 | 2/2011 | Ingber et al. |
| 2011/0150724 A1 | 6/2011 | Furle et al. |
| 2012/0105837 A1 | 5/2012 | Ingber |
| 2012/0309636 A1 | 12/2012 | Gibbons et al. |
| 2014/0170691 A1 | 6/2014 | Ingber et al. |

FOREIGN PATENT DOCUMENTS

| | | |
|---|---|---|
| JP | 6266141 A | 3/1987 |
| JP | 6465458 A | 3/1989 |
| JP | 1105849 U | 7/1989 |
| JP | 2254364 A | 10/1990 |
| JP | 4348250 A | 12/1992 |
| JP | 51989 A | 1/1993 |
| JP | 8122336 A | 5/1996 |
| JP | 2004203390 A | 7/2004 |
| JP | 2006349582 A | 12/2006 |
| JP | 2008501980 A | 1/2008 |
| JP | 200896115 A | 4/2008 |
| JP | 2008511815 A | 4/2008 |
| JP | 2011511942 A | 4/2011 |
| JP | 2011523073 A | 8/2011 |
| WO | 2004055522 A1 | 7/2004 |
| WO | 2005124365 A2 | 12/2005 |
| WO | 2007039524 A2 | 4/2007 |
| WO | 2007085715 A1 | 8/2007 |
| WO | 2009049171 A2 | 4/2009 |
| WO | 2009100197 A2 | 8/2009 |
| WO | 2011156915 A2 | 12/2011 |
| WO | 2012036296 A1 | 3/2012 |

* cited by examiner

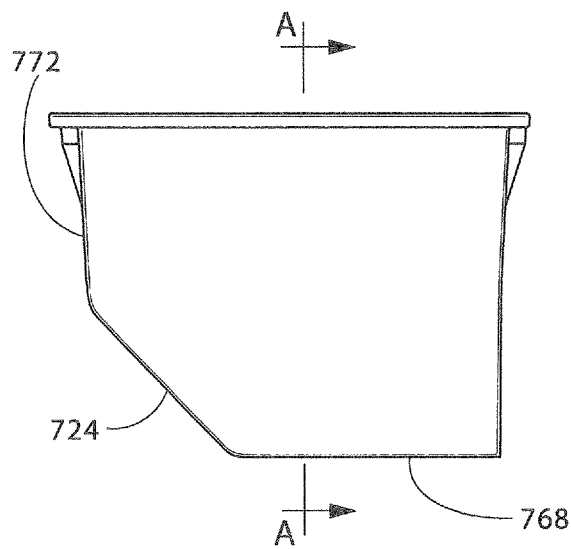
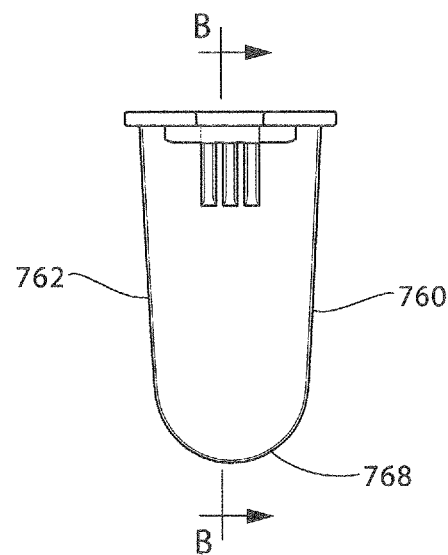
FIG. 8  FIG. 9
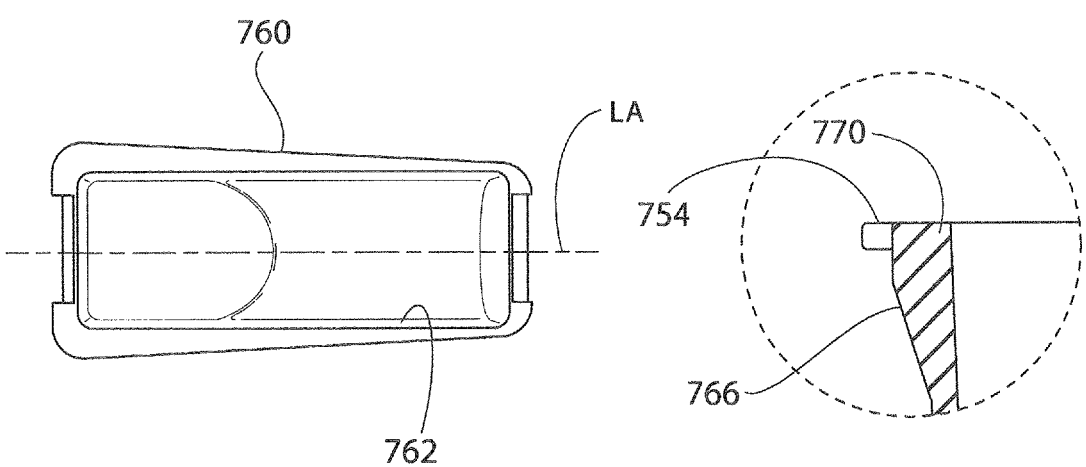
FIG. 12  FIG. 13

OPTICS CUP WITH CURVED BOTTOM

CROSS REFERENCE TO RELATED APPLICATIONS

This application is a divisional of U.S. patent application Ser. No. 14/102,742 filed Dec. 11, 2013 which claims the benefit of U.S. Provisional Application No. 61/735,737 filed Dec. 11, 2012, the disclosure of which is hereby incorporated in its entirety by reference.

BACKGROUND OF THE INVENTION

The present invention relates to a system for conducting the identification and quantification of micro-organisms, e.g., bacteria, in biological samples such as urine. More particularly, the invention relates to a system comprising a disposable cartridge and an optics cup or cuvette having a tapered surface. The system may utilize the disposable cartridge in a sample processor and the optics cup or cuvette in an optical analyzer, wherein the optics cup also has a floor in the shape of an inverted arch.

DESCRIPTION OF RELATED ART

In general, current-day practice for identifying micro-organisms, e.g., bacteria in urine samples, involves a complex, lengthy, and expensive process for identifying and specifying micro-organisms in microbiology labs. In the current process, the samples are accepted into the lab. These specimens are then sorted, labeled, and then they are inoculated onto blood agar medium using a sterilized loop. The specimens are then inserted into a dedicated incubator for a 24-hour period. A day later, the lab technicians screen the specimens for positive and negative cultures. In general, most of the cultures are negative and they are manually reported. The organisms for the positive cultures are isolated and suspended in a biochemical fluid. This involves suspension, dilution, vortexing, and turbidity measurements resulting in biochemical waste products. The cultures are then subjected to a species identification and antibiotics susceptibility testing exposing the suspensions to multiple reagents. After another 6 to 24-hour incubation period, the findings are interpreted and reported by lab technicians. This entire process generally takes 11 steps and 50 hours to obtain specimen results and the process is labor intensive.

Commonly owned U.S. Patent Application Publication No. US 2007/0037135 A1, the contents of which are herein incorporated by reference, discloses a system for identification and quantification of a biological sample suspended in a liquid. As disclosed in the reference, sample cuvettes are used for holding the biological sample. The reference states that these cuvettes are said to be well known in the art, are typically square or rectangular in shape (having a well area to contain the sample), and are made of a transparent material such as glass or a polymeric material. However, the reference fails to disclose any specific description/design of the cuvettes.

There is a need, therefore, particularly for species identification of the above lab procedure to provide an improved design for an optics cup or cuvette and a method for manufacturing the optics cup or cuvette or for holding samples, which optics cup or cuvette may be used in a system for an optical analysis of the sample, thereby allowing the process for species identification to be more efficient.

SUMMARY OF THE INVENTION

The present invention relates to such an optics cup or cuvette referred to above for holding a sample, e.g., biological sample, chemical sample, or toxicant sample, e.g. urine, for optical analysis. If the sample is a urine sample, then the optical analysis would be for micro-organism or organisms, e.g. bacteria, in the urine.

In one embodiment, an optics cup for holding a biological sample for use in an optical analysis has a generally rectangular-shaped container made of a transparent material and adapted to contain the biological sample. The container includes a pair of side walls having a longitudinal axis therebetween, a first end wall, and a second end wall spaced apart from the first end wall, and a floor. The container has a rectangular opening for receiving the biological sample and a lower tapered area extending from the first end wall inwardly and downwardly direction relative to the rectangular opening. The tapered area extends downwardly to the floor, wherein the floor has the shape of an inverted arch extending continuous along the entire length of the floor. The inverted arch is symmetric about the longitudinal axis.

In another embodiment, an optics cup for holding a biological sample for use in an optical analysis has a generally rectangular-shaped container made of a transparent material and adapted to contain the biological sample. The container includes a pair of side walls having a longitudinal axis therebetween, a first end wall, and a second end wall spaced apart from the first end wall, and a floor. The second end wall extends at an angle B3 of between 1°-3° with respect to a vertical axis extending through a meeting point between the floor and the second end wall. The container has a rectangular opening for receiving the biological sample and a lower tapered area extending from the first end wall inwardly and downwardly direction relative to the rectangular opening. The tapered area extends downwardly to the floor. The tapered area is angled at an angle of between approximately 43.5° and 44.5° relative to a vertical plane extending through the optics cup. The floor has the shape of an inverted arch extending continuous along the entire length of the floor. The inverted arch is symmetric about the longitudinal axis.

In an additional embodiment, a disposable cartridge for use in the identification and quantification of micro-organisms in biological samples has a plurality of compartments for positioning and supporting a plurality of disposable components including a centrifuge tube, a pipette and an optics cup adapted to contain the processed biological sample for use in an optical analysis. The optics cup has a generally rectangular shape with opposing sidewalls having a longitudinal axis therebetween and a tapered area extending from a first end wall of the optics cup into which a light source travels for the optical analysis of the processed biological sample. The cup also has a reflective surface for enhancing the optical analysis. The tapered area extends in a direction outwardly as the second end wall extends upwardly from the floor at an angle A5 of between approximately 43.5°-44.5° with respect to a vertical plane extending through the optics cup. The compartment for positioning and supporting the optics cup has a rectangular-shaped opening for receiving and supporting the rectangular-shaped optics cup. The tapered area of the optics cup extends downwardly to a floor. The floor has the shape of an inverted arch extending continuously along the entire length of the floor, and the inverted arch is symmetric about the longitudinal axis.

These and other objects and advantages of the invention will be made apparent from the following description taken together with the drawings.

BRIEF DESCRIPTION OF THE DRAWINGS

FIG. 8 is a side view of the optics cup of FIG. 7;

FIG. 9 is a front view of the optics cup of FIG. 8;

FIG. 12 is a top view of the optics cup of FIG. 7;

FIG. 13 is a detailed view of the snap portion on the flange denoted by I in FIG. 11;

DETAILED DESCRIPTION OF THE INVENTION

Figure 1:
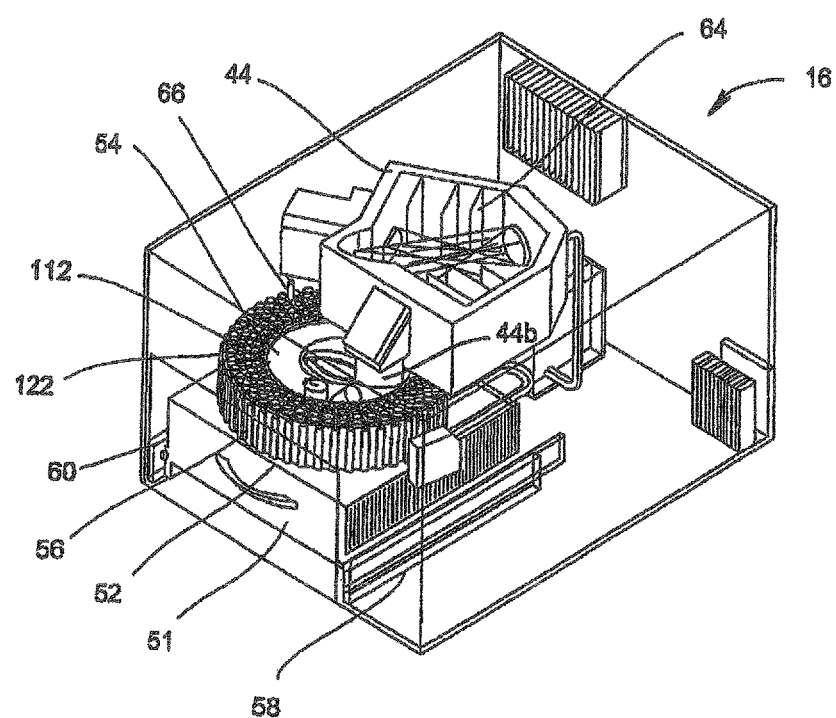
FIG. 1 is prior art and is a perspective view of an optical analyzer illustrating several components of an optical analyzer utilizing optics cups.

Commonly owned U.S. Patent Application Publication No. 2012/0105837, the content of which are herein incorporated by reference, discloses an optics cup for use in identifying and quantifying a biological sample suspended in a liquid. The present invention is directed to a specific optics cup having a floor in the shape of an inverted arch.

The present invention will be described with reference to the accompanying drawings where like reference numbers correspond to like elements.

For purposes of the description hereinafter, spatial or directional terms shall relate to the invention as it is oriented in the drawing figures. However, it is to be understood that the invention may assume various alternative variations, except where expressly specified to the contrary. It is also to be understood that the specific components illustrated in the attached drawings, and described in the following specification, are simply exemplary embodiments of the invention. Hence, specific dimensions and other physical characteristics related to the embodiments disclosed herein are not to be considered as limiting.

Figure 2:
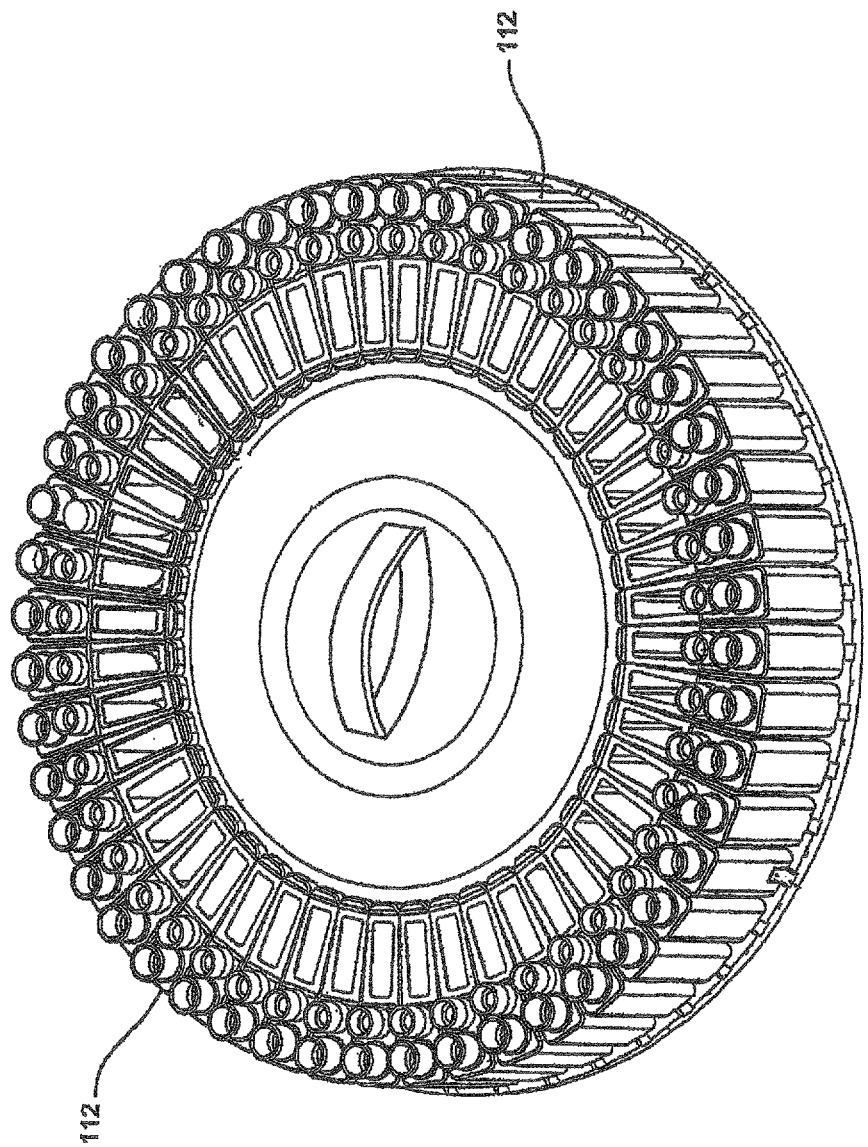
FIG. 2 is prior art and is a top perspective view of a magazine having a plurality of the disposable cartridges for holding optics cups.

FIG. 1 discloses "A System for Conducting the Identification of Bacteria in Urine" set forth in PCT Patent Application Publication No. US 2008/079533, filed on Oct. 10, 2008, which is commonly owned and herein incorporated by reference in its entirety. With reference to FIGS. 1 and 2, an optical analyzer 16 includes an optics system 44, a thermal control unit (not shown), a drawer 51 which has a rotatable table 52 which receives, supports, and rotates a magazine 54 containing a plurality of holders 56 for receiving the disposable cartridges 112 in which optics cups or cuvettes 22 contain the processed urine samples which are to be analyzed, and a bar code reader 58.

Referring to FIG. 1, an optics cup or cuvette 122 may be used in the optical analyzer 16. Preferably, urine samples are prepared with a saline solution since saline solutions minimize background fluorescence while maintaining the integrity of the bacteria which is particularly important when using optics in the urine analysis process. The optics cup or cuvette 12 will include a reflective coating to assist in the optical analysis. The optics cup or cuvette 12 may be made of an ABS plastic material, glass or a metallic material, e.g., aluminum, and then coated with or layered with the reflective material. Alternatively, in the manufacturing of the optics cup or cuvette 12, the layer of reflective material may be incorporated onto the plastic, glass or metallic material.

Figure 3:
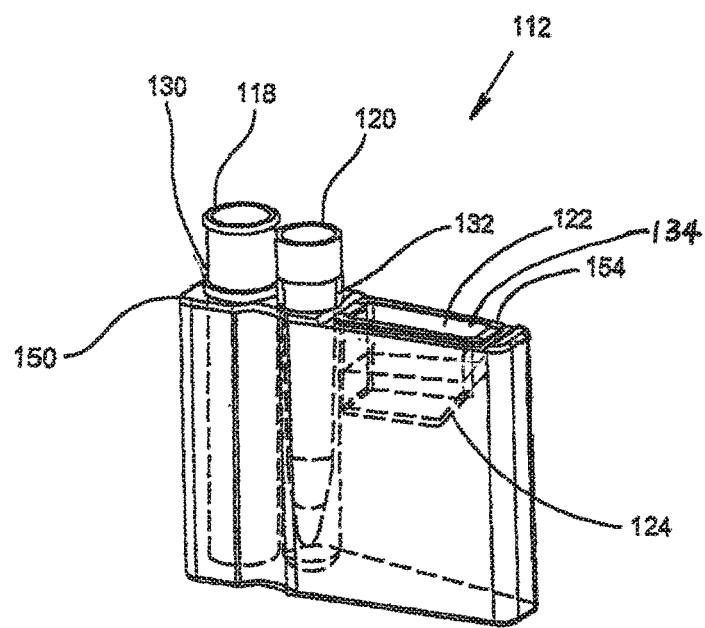
FIG. 3 is prior art and is a perspective view of a disposable cartridge for the magazine of FIG. 2 for supporting the disposable components including an optics cup.

As best shown in FIG. 3, the optics cup or cuvette 122 includes a tapered end indicated at 124 in order to assist with the optical analysis. It is anticipated that the UV-light source in the optical analyzer 16 (FIG. 1) be directed down the middle of the cup or cuvette 122 for the optical analysis of the urine specimen in the cup or cuvette 122.

Returning to FIG. 1, the optics system 44 will include a light-tight enclosure or housing 64 in order to minimize light entering the optics system 44, and the camera of the CCD device will include a thermal electric cooler (TEC) (not shown) for transferring heat from the camera chip to the enclosure or housing 64 of the optics system 44.

FIG. 3 illustrates an embodiment for a disposable cartridge generally indicated as 112, which may be used for conducting the identification and quantification of contaminants, e.g., micro-organisms, e.g., bacteria in samples, e.g., urine samples. Disposable cartridge 112 contains and carries several disposable components which include a centrifuge tube 118, a pipette tip 120, and the optics cup or cuvette 122. The pipette tip 120 has a predetermined volume, for example, ranging between 0.1 ml to about 10 ml, preferably 1 ml to 2 ml. The centrifuge tube 118 is a container that has an elongated body with a tapered end. In general, the centrifuge tube 118 initially contains the sample and the pipette tip 120 may be used to dilute the dissolved sample constituents and then transfer the diluted urine sample into the optics cup or cuvette 122 for optical analysis. The disposable cartridge 112 and its disposable components 118, 120, 122 may be made of an ABS plastic material which is easily injection molded and inexpensive to manufacture and made of an ABS plastic, preferably a non-reflective black colored plastic.

Still referring to FIG. 3, the disposable components 118, 120, 122 are each contained within separate compartments 130, 132, 134, respectively, of the disposable cartridge 112. An optics cup or cuvette 122 is suspended within its respective compartment 134 via a flange 154 of the optics cup or cuvette 122, which the flange 154 is supported by the top surface 150 of disposable cartridge 112. The compartments 130, 132 are generally cylindrical-shaped and extend substantially the length of centrifuge tube 118 and pipette tip 120. Compartment 134, for positioning supporting optics cup or cuvette 122, is substantially enclosed within the disposable cartridge 112 and has a configuration similar to that of optics cup or cuvette 122.

Figure 4:
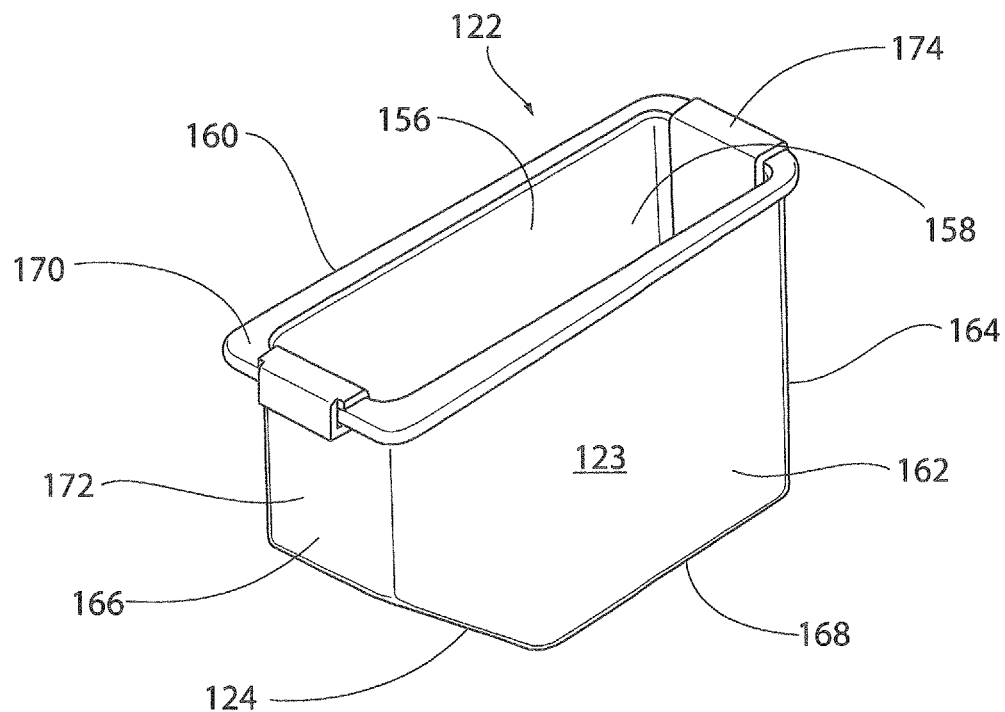
FIG. 4 is prior art and is a perspective view illustrating an optics cup with an aluminum ribbon liner partially covering the inner surface of the container of the optics cup and a flat straight bottom.
Figure 5:
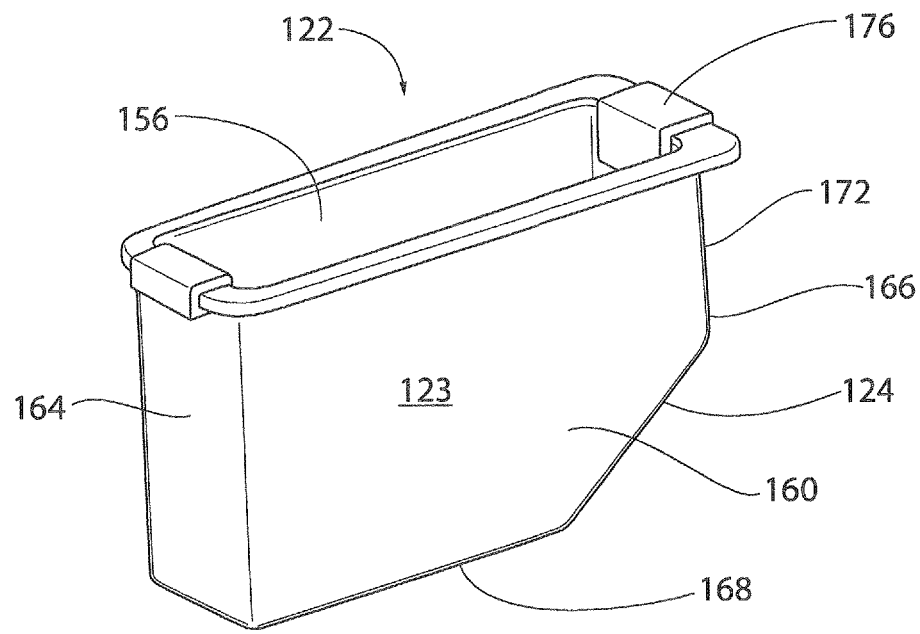
FIG. 5 is prior art and is a perspective view illustrating an optics cup with an aluminum liner totally covering the inner surface of the container and a flat straight bottom.

The optics cup or cuvette 122 is a container and preferably includes a reflective coating or layer to assist in the optical analysis. The optics cup or cuvette 122 is also shown in FIGS. 4 and 5 and is discussed in further detail below. In particular, an inner surface of optics cup or cuvette 122 is coated with a reflective material or contains a layer of reflective material. The optics cup or cuvette 122 may be made of a non-reflective material, for example, an ABS plastic material or glass, or it may be made of a metallic material, e.g., aluminum. In the latter instance, that is, if the optics cup or cuvette 122 is made of a non-reflective material, it may be coated with or layered with the reflective material. Alternatively, in the manufacturing of the optics cup or cuvette 122, the layer of reflective material may be incorporated onto the plastic or glass. As best shown in FIG. 4, the optics cup or cuvette 122 includes the lower tapered area indicated at 124 in order to assist with the optical analysis of the specimen, and it is anticipated that the UV-light source provided in an optical analysis be directed into the optics cup or cuvette 122 for the optical analysis of the specimen, more about which is discussed herein below.

The compartment 134 (FIG. 3) for positioning and supporting the optics cup or cuvette 122, particularly if the optics cup or cuvette 122 is rectangular-shaped, need not be molded in the same configuration as the optics cup or cuvette 122. In this instance, the compartment 134 for supporting the optics cup or cuvette 122 in the disposable cartridge 112 may, in general, include a rectangular-shaped opening 158 (FIG. 3) located in the top surface 150 of the disposable cartridge 112, wherein the top flange 154 of optics cup or cuvette 122 engages and is supported by the top surface 150 of the disposable cartridge 112 and the optics cup or cuvette 122 is suspended in the disposable cartridge. Alternatively, the compartment 134 for positioning and supporting the optics cup or cuvette 122 may be totally enclosed and may have a similar configuration to that of the rectangular-shaped optics cup or cuvette 122.

FIGS. 4 and 5 are prior art and illustrate an optics cup or cuvette, generally indicated as 122, including a rectangular-shaped container 123 having a well 156 and a rectangular opening 158 contiguous to the well 156 for receiving a fluid sample, which is then carried in the well 156. As stated above, the optics cup or cuvette 122 may be made of glass or plastic, preferably, an injection molded plastic. The fluid sample may be, for example, a biological, chemical, or toxicant sample, e.g., urine sample, which is optically analyzed, for example, for the type and amount of organism or micro-organism, e.g., bacteria, in the sample. The well 156 of the container 123 is formed by spaced-apart sidewalls 160, 162, spaced-apart first end wall 166, second end wall 164, and a floor 168. The spaced-apart sidewalls 160, 162 and spaced-apart first and second end walls 166, 164 form a flange 170 contiguous to the rectangular opening 158. As shown in FIGS. 4 and 5, the first end wall 166 has an upper area 172 and a lower tapered area 124 extending inwardly of the upper area 172 of end wall 166 and downwardly relative to upper area 172 of the end wall 166 and the rectangular opening 158, such that the length of the floor 168 is less than the length of the rectangular opening 158.

With particular reference to FIG. 4, the optics cup or cuvette 122 also includes a ribbon liner 174 which extends the full length of end wall 164, floor 168, upper area 172 of end wall 166, and lower tapered area 124 of end wall 166 to cover the inner surfaces of end wall 164, floor 168, upper area 172 of end wall 166, and lower tapered area 124 of end wall 166. The ribbon liner 174 may be referred to as a "wet" ribbon liner since it comes into contact with the liquid sample from all sides. The ribbon liner 174 is preferably made of a reflective material, for example, aluminum. The ribbon liner 174 may be made from a piece of stamped aluminum which may be pre-shaped to conform to the configuration formed by end wall 164, floor 168, lower tapered area 124 of end wall 166, and upper area 172 of end wall 166 prior to the installation of ribbon liner 174 in well 156.

Figure 6:
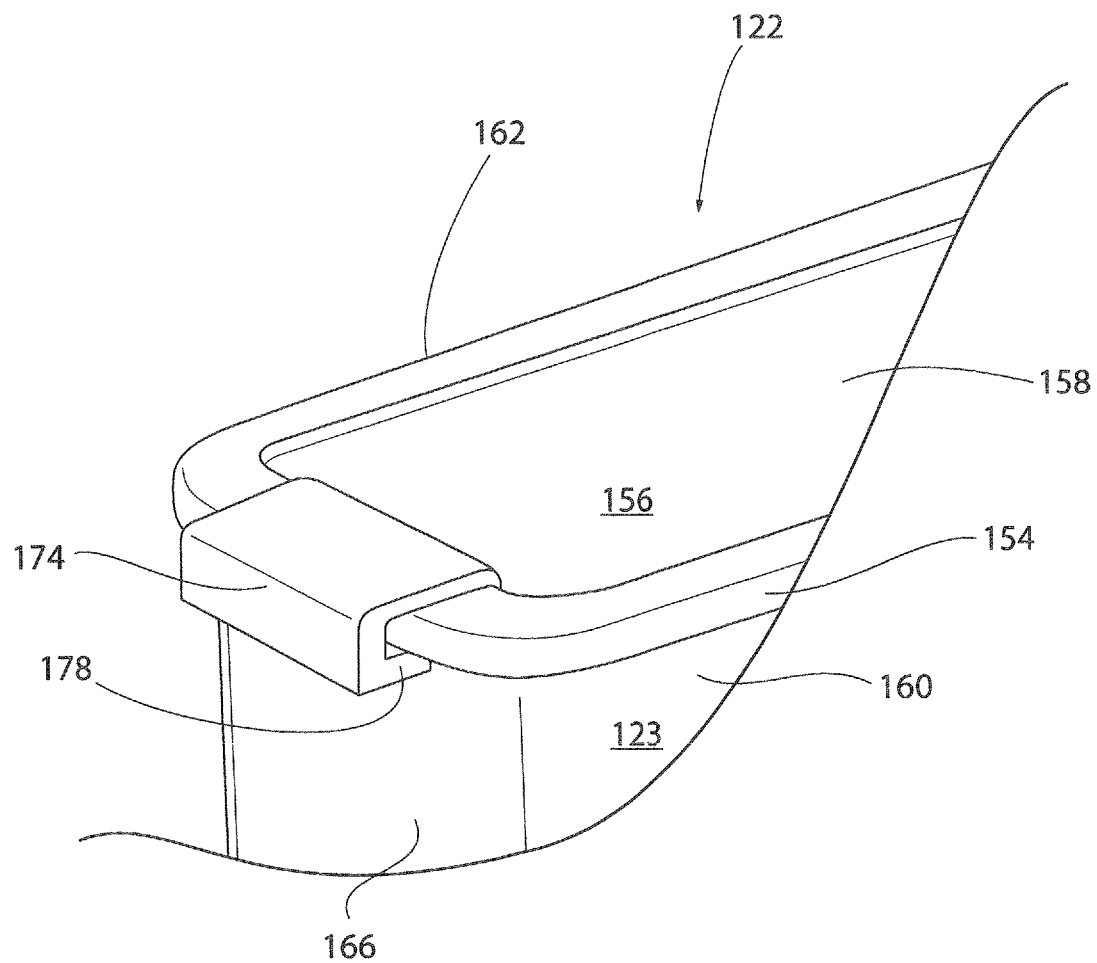
FIG. 6 is prior art and is a partially enlarged perspective view illustrating a portion of the ribbon liner of FIG. 4 attached via a crimping process to a flange of the optics cup of the present invention.
Figure 7:
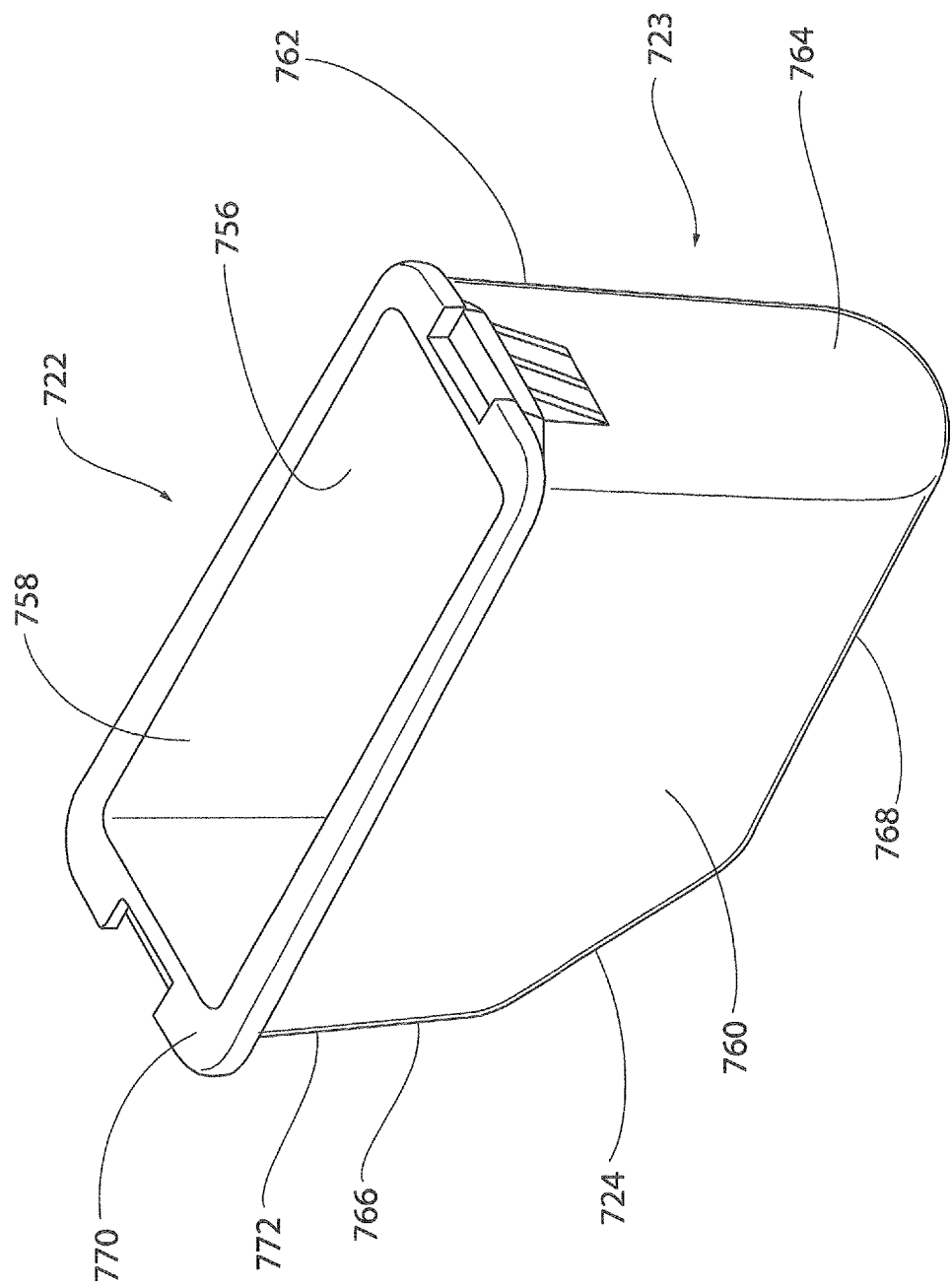
FIG. 7 is a front perspective view illustrating an optics cup according to one embodiment of the present invention.

FIG. 6 illustrates that the wet ribbon liner 174 of FIG. 4 may be secured to optics cup or cuvette 122 via a crimping process. In this instance, the one end 178 of the wet ribbon liner 174 is bent to conform around and under the outer contour of the portion of flange 154 formed by end wall 166 and end 178 is fastened to flange 154 via a crimping process, which is well known to those skilled in the art. Even though not shown in FIG. 6, it is to be appreciated that the opposite end of ribbon liner 174 may be bent to conform around and then under the outer contour of the portion of flange 154 formed by end wall 164 and then fastened to flange 154 via a crimping process.

The optics cup or cuvette 122 may be made of a material known to minimize the leaching of the contaminants from the material that might be excited by the incident light used in an optical analysis of the sample. As stated above, the optics cup or cuvette 122 may be injection molded and made of a material, for example, ABS plastic or glass. It is anticipated that the UV light provided in an optical analysis of the sample or specimen in container 123 of optics cup or cuvette 122 be directed into the tapered area 124 of the well 156 for the optical analysis of the specimen and be reflected off of the ribbon liner 174, including the lower tapered area 124 of end wall 166. As discussed herein above, the material of the optics cup or cuvette 122, the reflective material of ribbon liner 174 and the lower tapered area 124 of end wall 166 work in a synergistic manner to enhance the UV-light reflection to more effectively collect the fluorescence emission of the samples for the identification and quantification of the organism or micro-organism, e.g., bacteria in the samples and, at the same time, minimize the background fluorescence and/or minimize the contamination of the sample fluid from the container or wetted surfaces of the container. The collection of the fluorescence emission of the sample from the optic cup or cuvette 122 is discussed in greater detail below.

Figure 10:
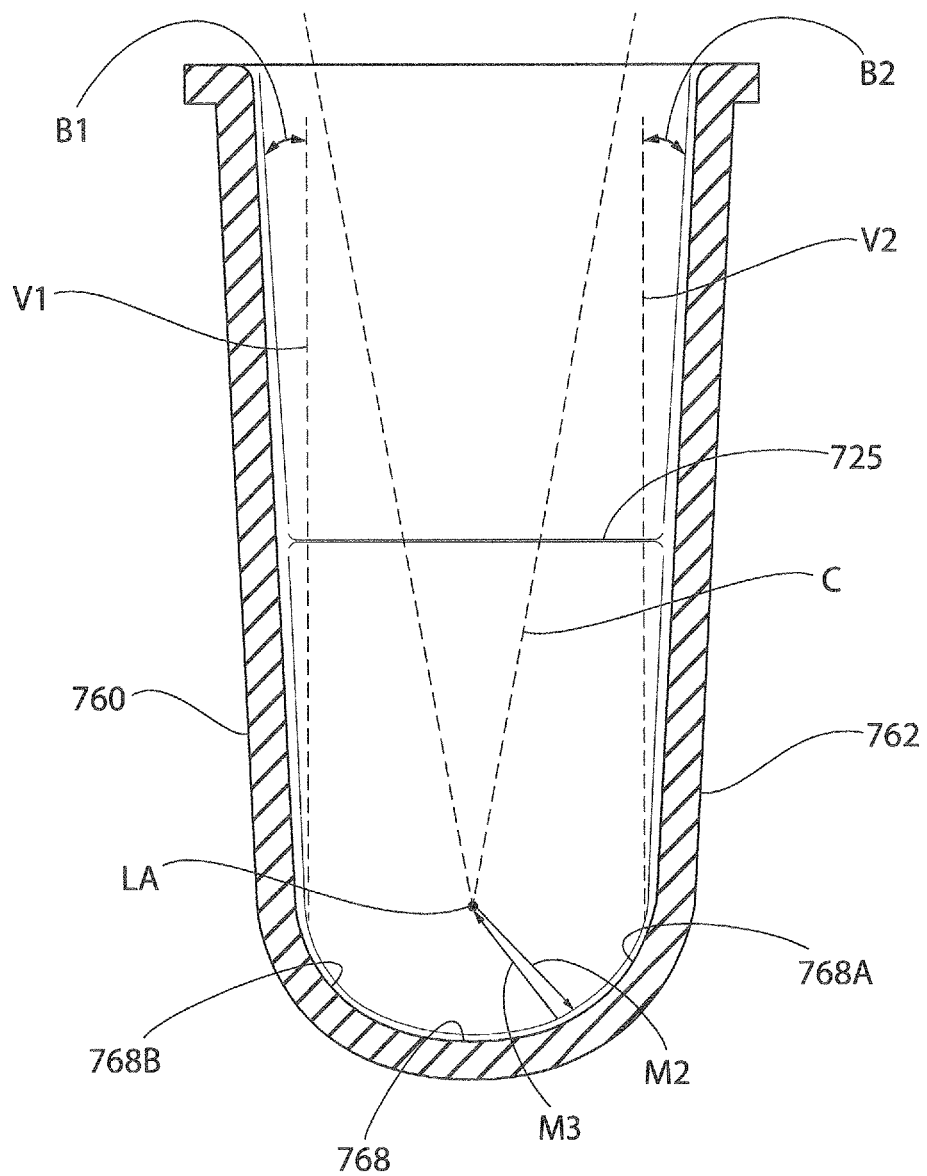
FIG. 10 is a cross-sectional view taken along lines "A-A" in FIG. 8.
Figure 11:
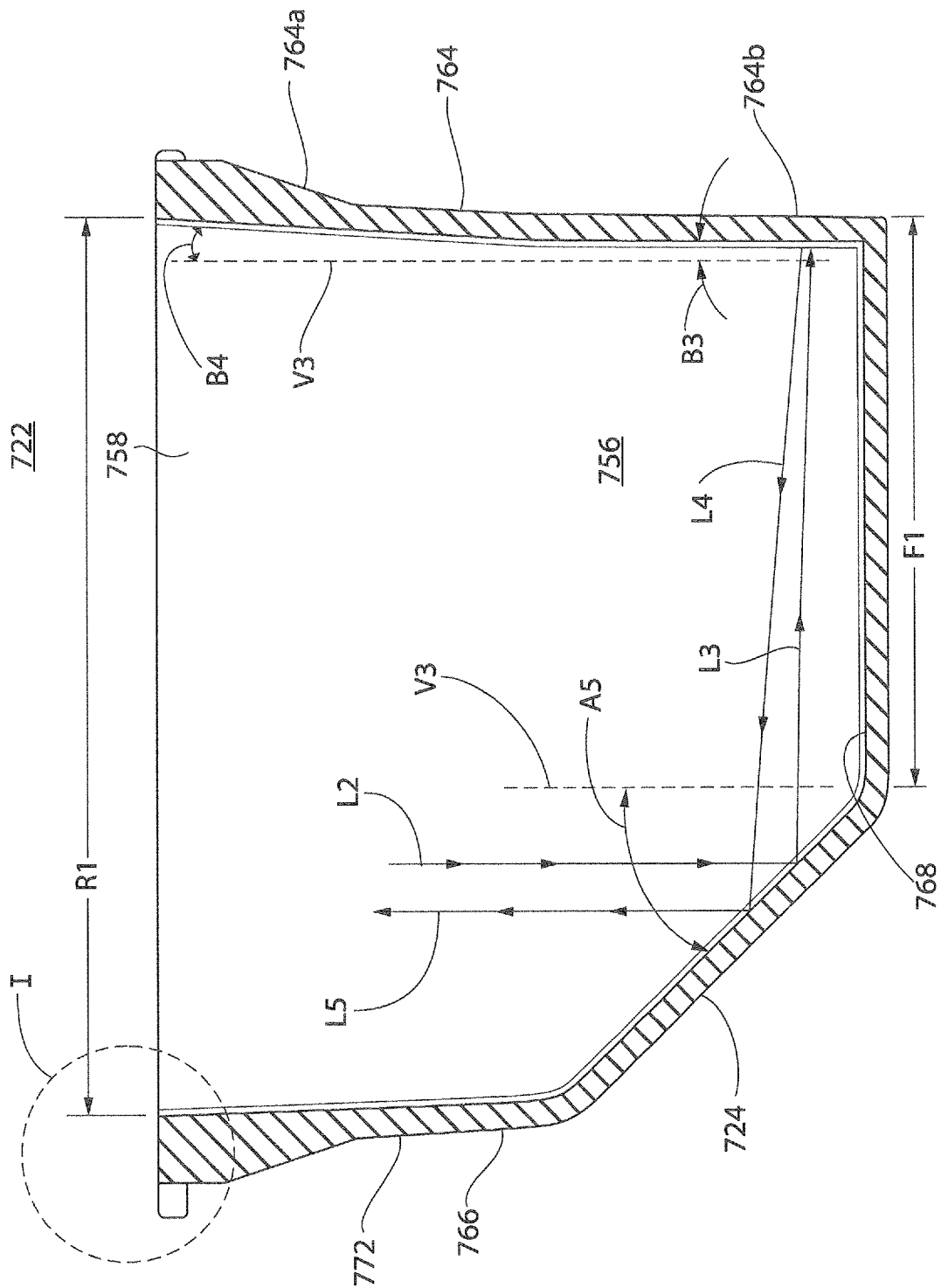
FIG. 11 is a cross-sectional view of the optics cup taken along line "B-B" of FIG. 9.

FIGS. 7-13 illustrate an optics cup or cuvette, according to one embodiment of the invention, generally indicated as 722. The optics cup or cuvette 722 includes a rectangular-like shaped container 723 having a well 756 and a rectangular opening 758 continuous to the well 756 for receiving a fluid sample which is then carried in the well 756. Similar to the previously discussed optics cup or cuvette 122, the optics cup or cuvette 722 may be made of glass or plastic. The fluid sample to be received into the well 756 may be, for example, a biological, chemical or toxicant sample, e.g., urine sample, which is optically analyzed, for example, for the type and amount of organism or micro-organism, e.g., bacteria, in the sample. The well 756 of the container 723 is formed by spaced-apart side walls 760, 762, spaced-apart first end wall 766 and second end wall 764, and a floor 768. The spaced-apart side walls 760, 762 form a flange 770 contiguous to the rectangular opening 758. As shown in FIG. 11, the first end wall 766 has an upper area 772 and a lower tapered area 724 extending inwardly of upper area 772 of end wall 766 and downwardly relative to upper area 772 of first end wall 766 and the rectangular opening 758, such that the length F1 of floor 768 is less than the length R1 of the rectangular opening 758.

The dimensions of the optics cup or cuvette 722 in the embodiment of FIGS. 10 and 11 are such that diversion and striations of the straight light beam have been optimized. In particular, as shown in FIG. 10, the opposed side walls 760, 762 form an angle B1, B2, which may be 3° in a direction extending outwardly as the side walls 760, 762 extend upwardly from the floor 768 with respect to vertical lines V1, V2 respectively. The angles B1, B2 are measured from a location or fill-line 725 where the top of a sample would be located within the optics cup or cuvette. The total offset angle between the side walls 760, 762 may equal approximately 6°. Angling of the side walls 760, 762 allows for better coating with a reflective material, such as aluminum material as discussed below. As shown in FIG. 11, the second end wall 764 has a top portion 764a and a bottom portion 764b. The bottom portion 764b can be angled at an angle B3 of between 1°-3° in a direction extending outwardly as the end walls 764, 766 extend upwardly from the floor 768 with respect to vertical line V3 extending through the bottom of the optic cup or cuvette 722. At the location on fill-line 725, where the top portion of a sample would be located in the optics cup or cuvette 122, the top portion 764a of the second end wall 764 can have an additional 2° angle forming a total angle B4 of between 3°-5° with respect to the vertical line V3 in a direction extending outwardly as the side walls 760, 762 extend upwardly from the floor 768. The angle A5 between the tapered area 724 and the bottom portion 764b of the second end wall 764 extends at approximately 45.5°. The angle of the tapered area also extends at approximately between 44.5°-45.5° with respect to the vertical plane V3 extending through the optics cup. This angled tapered area 724 supports accurate beam travel back and forth as depicted by L2-L5.

A primary difference between the prior art cuvette 122 and the cuvette 722 according to the present invention is that the floor 168 of the cuvette 122, as illustrated in FIG. 5, is flat while the floor 768 of the cuvette 722, as illustrated in FIG. 9, is curved. Additionally, the relative angles of the walls are difference along with other features to be discussed.

Additionally, as illustrated in FIGS. 8 and 9, the floor 768 of the optics cup 722 has the shape of an inverted arch extending continuously along the entire length of the floor 768. Furthermore, the inverted arch is symmetric about and uniform along a longitudinal axis LA (FIGS. 10 and 12) extending between the side walls 760, 762. As a result, the inverted arch is oriented such that light inside the illuminated cup travelling away from the optical collection cone C (FIG. 10) will be reflected to the collection point. By doing so, the amount of collected light will be increased. For example, as illustrated in FIG. 10, light travelling along the path M2 will be reflected to the collection point along line M3. Lines M2 and M3 are actually overlapping but shown apart for illustrative purposes.

The arch of the floor may have a single radius of curvature along the entire length or the curvature may vary, such as the curvature found in an ellipse. However, it is necessary for the curvature to be symmetrical about the longitudinal axis LA.

As shown in FIG. 11, the lower taper area 724 is oriented with respect to the second end wall 764 such that an incoming illumination beam, illustrated by line L2, will hit and reflect, illustrated by line L3, from the lower taper area 724 to the lower portion 764b of the second end wall 764, where it will be reflected back along line L4 to the lower taper area 724, where it is reflected back along line L5. As a result, it is preferred that the deviation from a 45° angle of the angle A5 of the lower taper 724 is one-half the deviation of the angle B3 of the bottom portion 764b of the second end wall 764 from a vertical axis V3. As a result, the illuminating beam will travel into the cup 722, reflect from the cup 722 along a parallel path and will not illuminate the bottom of the cup 722.

As an example, at the location or fill-line 725, where the top portion of a sample would be located in the cup or cuvette 122, the lower portion 764b of second wall 764 is angled at an angle B3 of approximately 1°. Therefore, designing the angle A5 of the tapered area 724 of the first wall 766 such that it extends at a 44.5° angle with respect to the plane or line V3, causes light beam L2 to contact tapered wall 764b and redirect that light beam along path L3 where it reflects back from the bottom portion 764(b) and once again, contacts the lower tapered area 724 and is directed along line L5. The 44.5° angle of the lower tapered area 724, with respect to vertical plane V3, prevents skewing or misdirection of the light beam within the sample.

As illustrated in FIG. 11, the bottom portion 764b may form an angle B3 of 1°, with respect to the vertical line V3, while the top portion 764a may form an angle B4 of 3°, with respect to the vertical line V3. For better surface quality, when molding the cup 722, it may be desirable to design the top portion 764a and bottom portion 764b as a single planar surface. Under these circumstances, the bottom portion 764b would be oriented at an angle B4 of 3° and aligned with the top portion 764a, thereby providing such a single planar surface. Such a single planar surface, while not illustrated in the figures, may be easily envisioned from examination of FIG. 11. However, under these circumstances, to ensure the transmitted illumination beam L2 will reflect back upon line L5, the orientation of the lower taper area must also be changed to provide, for example, a surface with an angle A5 of 43.5°.

Location of the snap features which are used to hold the cup within its location in the cartridge with respect to the longitudinal axis of the optics cup or cuvette 722 is important to the beam location inside the volume since the beam location on the angle surface as measured from the top edge of that surface will determine the beam location from the bottom surface. The total area of the bottom floor 768 of the well 756 can be approximately 84 mm$^2$. In a preferred embodiment, the snap feature is located on the side of the cuvette with the first end wall 766, as illustrated in FIG. 13.

Figure 14:
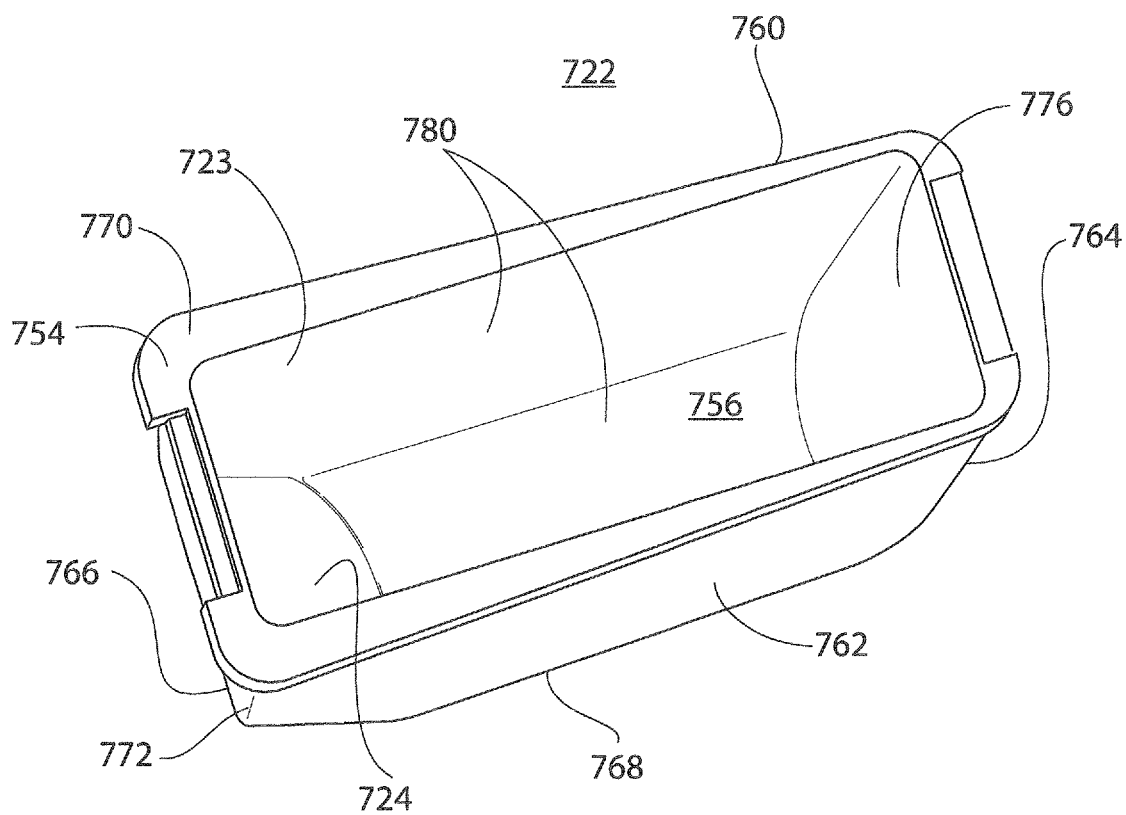
FIG. 14 is a top perspective view illustrating the inner surface of the container of FIGS. 4 and 5 as being coated with an aluminum coating.

FIG. 14 illustrates that alternatively, the optics cup or cuvette 722 may include a full liner 776, if light collection from the sidewalls 760 and 762 as well as from the end wall 764, floor 768, the lower tapered area 724 of end wall 766 and the upper area 772 of end wall 766 is needed for the optical analysis of a sample. This full liner 776 is shaped and formed to substantially clad or cover the inner surfaces of sidewalls 760, 762, end wall 764, floor 768, lower tapered area 724 of end wall 766, and the upper area 772 of end wall 766. The full liner 776 of FIG. 14 functions similarly to the ribbon liner 174 in the well 156 of the optics cup or cuvette 122 of FIG. 4 with regard to the UV-light of the optical analyzer.

The full liner 776 of FIG. 14 may be polished to obtain a desired degree of surface roughness for the reflection of the UV-light in optics cup or cuvette 722. The polishing process may either be performed on the reflective material used to form wet ribbon liner, similar to liner 174 in FIG. 4, or full wet liner 776 either when the reflective material, i.e., aluminum is in raw sheet form prior to the stamping and forming process or when the liners 776 are formed and inserted into the optics cup or cuvette 722 via a bulk polishing process. That is, the reflective material may either be polished before the stamping and forming process or the stamped parts may be polished.

It is to be further appreciated that even though not shown, in the instance a full liner 776 of FIG. 14 is installed in the optics cup or cuvette 722, that this liner 776 may be secured to the flange 754 via a crimping process. The full liner 776 may be stamped and folded in a progressive die and then singulated for installation in the optics cup or cuvette 122. Both a ribbon liner and full liner 776 may be wound on a reel and the optics cup or cuvette 722 can be easily assembled in an automated manufacturing process. That is, both a ribbon liner and full liner 776 may be on a reel so that a machine can be fed with the reels and the liners inserted into the optic cups or cuvettes 122.

FIGS. 4 and 5 illustrate a reflective material for the optics cup or cuvette 122 as being a separate piece that is manufactured, formed and shaped for insertion or installation into the well 156 of the container 123. The present invention envisions that instead of the liners 174, 176, the optics cup or cuvette 722 may be coated with a thin layer of reflective material as indicated at reference number 780 in FIG. 14. In this embodiment, the optics cup or cuvette 122 may be injection molded with the desired surface roughness and then coated with a thin layer of reflective material 180, for example, pure aluminum, by either a vacuum metallization process or by an electroplating process. The industry has shown that it may be difficult to coat inner surfaces of a container that has a certain depth. In this instance, customized electrodes may need to be provided to achieve the desired coverage and uniformity of coating in the well 756 of the container 723 of the optics cup or cuvette 722. The coating of reflective material 780 may extend totally along the inner surfaces of sidewalls 760, 762, end walls 764, 766 and floor 768 of container 723 similar to the full liner 776 of FIG. 14 or the coating may extend partially along the inner surfaces of end wall 764, the floor 768, lower tapered area 724 of end wall 766, and the upper area 772 of end wall 764 of the container 723 similar to the ribbon liner 174 of FIG. 4.

Figure 15:
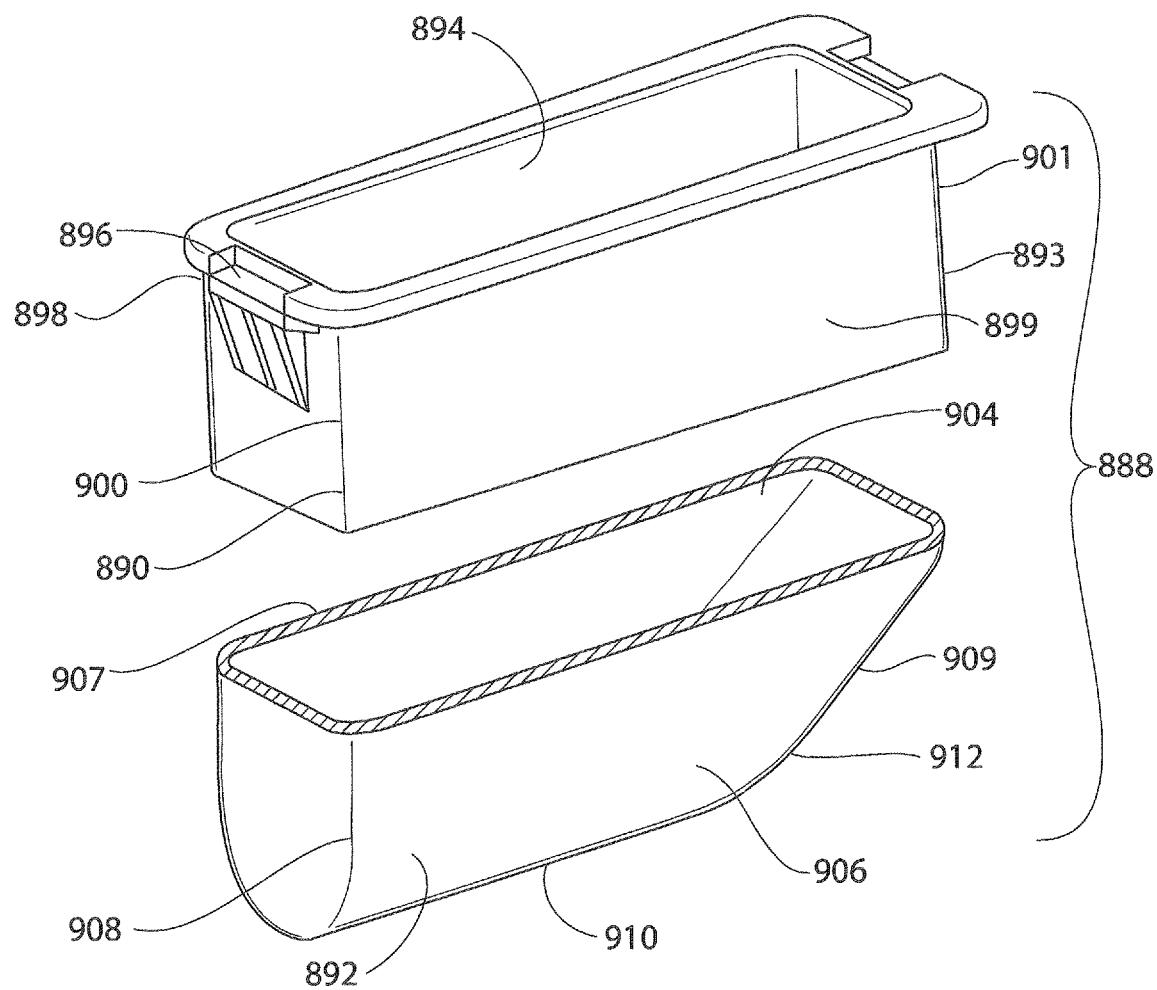
FIG. 15 is a perspective view illustrating a further embodiment for a rectangular-shaped container in the present invention.

FIG. 15 illustrates an optics cup or cuvette 888 having a two-piece construction including an upper piece 890 and a lower piece 892. As shown, the upper piece 890 has a rectangular body 893 having a rectangular opening 894 contiguous to the flange 896, which in turn, is formed by spaced-apart sidewalls 898, 899 and end walls 900, 901. Even though not shown, the upper piece 890 is also fully opened at the bottom and has an indented portion. The lower piece 892 has a rectangular opening 904 formed by spaced-apart sidewalls 906, 907 and end walls 908, 909, and a floor 910. The end wall 909 of the lower piece 892 has a tapered area 912 for re-directing the light. The tapered area 912 extends down from the rectangular opening 894 and extends downwardly to the floor 910, thereby making the length of the floor 910 less than the length of the rectangular opening 904.

As may be appreciated, the upper flanges of the optics cup or cuvette 722 of the present invention may be used for supporting the optics cup or cuvette 722 on a top surface 150 of a disposable cartridge 112 used in magazines 126 (FIG. 2) for processing the samples and then optically analyzing the samples. Also, the reflective surfaces of the optics cup or cuvette 722 are such that the UV light from the optical analyzer can be directed down into the cups or cuvettes and reflected off of the reflective surfaces and tapered areas as discussed in detail below to more efficiently and effectively produce the fluorescence emission necessary in obtaining the required information for optically analyzing the specimens for the identification and quantification of, for example, organisms or micro-organism, e.g., bacteria in the specimens, e.g., urine specimens.

It will be understood by one of skill in the art that the fluid sample may be, for example, a biological, chemical or toxicant sample, e.g., urine sample, which is optically analyzed, for example, for the type and amount of organism or microorganism, e.g., bacteria, in the sample.

The present invention has been described with reference to the preferred embodiments. Obvious modifications and alterations will occur to others upon reading and understanding the preceding detailed description. It is intended that the invention be construed as including all such modifications and alterations.

The invention claimed is:

1. A disposable cartridge for use in the identification and quantification of micro-organisms in biological samples, comprising:
    the disposable cartridge including an optics cup contained in a compartment for positioning and supporting the optics cup, wherein the optics cup is adapted to contain the biological sample for use in an optical analysis;
    the optics cup having a generally rectangular shape with a top rectangular opening, with a pair of opposing sidewalls having a longitudinal axis therebetween and a first end wall and a second end wall and a floor, wherein a lower tapered area extends from the first end wall in an inwardly and downward direction toward the floor relative to the rectangular opening of the optics cup, wherein the second end wall opposes the first end wall and extends upwardly away from the floor;
    the compartment for positioning and supporting the optics cup having a rectangular-shaped opening for receiving and supporting the optics cup;
    wherein the floor has the shape of an inverted arch extending along the entire length of the floor,
    wherein the inverted arch is symmetric about and uniform along the longitudinal axis and the inverted arch is curved;
    wherein a portion of the container along at least the tapered area is reflective for reflecting illumination introduced into the top opening and for light collection to enhance optical analysis of the biological sample, and
    wherein the arch is oriented such that the light inside the illuminated cup traveling away from an optical collection cone will be reflected to collection points along the longitudinal axis.

2. The disposable cartridge according to claim 1, wherein the disposable cartridge includes a compartment for receipt of a pipette tip.

3. The disposable cartridge according to claim 1, wherein the compartment for positioning and supporting the optics cup is substantially enclosed within the disposable cartridge.

4. The disposable cartridge according to claim 1, including at least one attachment clip configured for cooperating with a magazine opening for attaching the cartridge therein.

* * * * *